United States Patent [19]

Leneuf

[11] 4,116,991

[45] Sep. 26, 1978

[54] HYDROXY-CONTAINING AGENTS FOR CHELATING METAL IONS AND A PROCESS FOR PREPARING SAME

[75] Inventor: Andre Leneuf, Tours, France

[73] Assignee: Manufacture de Produits Chimiques Protex, Paris, France

[21] Appl. No.: 567,528

[22] Filed: Apr. 14, 1975

[30] Foreign Application Priority Data

Apr. 12, 1974 [FR] France .................. 74 13622

[51] Int. Cl.$^2$ ............................................. C07F 15/02
[52] U.S. Cl. ............................ 260/439 R; 260/429 C; 260/429 J; 260/464; 260/465 D; 260/465 E; 260/566 F; 260/509; 562/451; 260/574; 562/448
[58] Field of Search ................. 260/429 J, 439 R, 519

[56] References Cited

U.S. PATENT DOCUMENTS

| | | | |
|---|---|---|---|
| 2,921,847 | 1/1960 | Knell et al. | 260/439 R X |
| 3,095,297 | 6/1963 | Rembe | 260/439 R X |
| 3,248,410 | 4/1966 | Berenbaum | 260/429 J |
| 3,567,752 | 3/1971 | Israily | 260/439 R |
| 3,592,830 | 7/1971 | Israily | 260/439 R |
| 3,711,525 | 1/1973 | Hennart | 260/439 R |
| 3,780,099 | 12/1973 | Scanlon | 260/429 J |
| 3,780,100 | 12/1973 | Scanlon | 260/429 J |

Primary Examiner—Helen M. S. Sneed
Attorney, Agent, or Firm—Karl F. Ross

[57] ABSTRACT

A chelating agent of the formula:

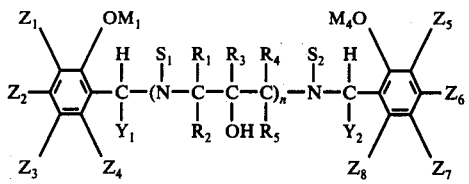

wherein $R_1$ through $R_5$ are each selected from the group which consists of hydrogen, methyl, ethyl and propyl;

$S_1$ and $S_2$ are each selected from the group which consists of hydrogen, $-CH_2CH_2OH$ and alkyl having 1 to 12 carbon atoms;

$n$ is a whole number 1 through 4;

$Z_1$ through $Z_8$ are substituents each selected from the group which consists of alkyl, alkoxyl, carboxy, formyl, acyl, carboxy substituted by alkyl, carboxamido, hydroxyl, amino, nitro, halo, and sulfo;

$Y_1$ is selected from the group which consists of $-COOM_2$ and $-CN$;

$Y_2$ is selected from the group which consists of $-COOM_3$ and $-CN$; and $M_1$ through $M_4$ are selected from the group which consists of hydrogen, ion, an alkali metal ion, ammonium and ammonium substituted by alkyl 1 to 4 times.

1 Claim, No Drawings

HYDROXY-CONTAINING AGENTS FOR CHELATING METAL IONS AND A PROCESS FOR PREPARING SAME

The subject of this invention is chelation agents and their chelates.

It is known to use iminopolyacetic acids to make complex compounds of divalent and trivalent metals for agricultural, industrial, and domestic purposes.

The acids in current use according to the present state of the art are:
ethylenediamine triacetic acid
imino-triacetic acid
diethylenetriamine penta-acetic acid
N-hydroxyethylethylenediamine triacetic acid
propanoldiamine-tetra-acetic acid
with their chelates, in order to remedy metallic deficiencies ascertained to exist in crop farming; however, although these products are potent in acid soils, their effectiveness is poor in alkaline soils on account of the instability of the chelate bonds so formed, in an alkaline environment.

It is also known to use chelation agents containing aromatic hydroxyl groups, offering better chelate stability in an alkaline environment. These agents, however, have the disadvantage that they are difficult to manufacture, particularly because of hydrolysis difficulties with the corresponding nitriles.

The present invention aims to remedy the drawbacks of the agents aforesaid by providing aromatic chelation agents containing a hydroxyl group at the center of the molecule.

These chelation agents have as the formula:

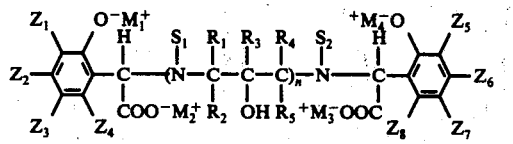

in which:

$R_1$ to $R_5$ are hydrogen, or alkyl groups of low molecular weight: especially methyl, ethyl or propyl, $S_1$ and $S_2$ are hydrogen, or a $CH_2CH_2OH$ group, or alkyl having 1 to 12 carbon atoms, $n$ is a small whole number, 1, 2, 3 or 4, $Z_1$ to $Z_8$ are hydrogen or a substituent group, alkyl, alkoxyl, carbonyl, hydroxyl, amino, nitro, halogen or sulpho, which cannot be hydrolyzed and is not capable of impeding the synthesis reaction described.

$M_1$ to $M_4$ are hydrogen, an alkali metal, or ammonium with 1 to 4 alkyl substitutions.

These chelation agents have chelating properties over a pH range extending far into the alkaline region, particularly with iron, which makes them suitable for the preparation of chelates of iron allowing plants subject to chlorosis to be grown in soils from which they have hitherto been entirely excluded, or to make it practicable to cultivate them in regions where, on account of alkalinity, this has not been done until now.

Moreover these agents are easily manufactured, for the hydrolysis of the corresponding nitrile only requires conventional products such as commercial hydrochloric acid, while until now it has required mixtures to be used which, on account of their high content of hydrogen halides, are unstable.

Chelating agents corresponding with formula (1) may be prepared in two different ways, by the glyoxylic route and by the hydrocyanic route.

More particularly, the invention relates to a compound of the following formula:

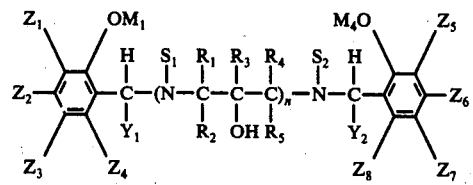

wherein $R_1$ through $R_5$ are each selected from the group which consists of hydrogen, methyl, ethyl and propyl;

$S_1$ and $S_2$ are each selected from the group which consists of hydrogen, $-CH_2CH_2OH$ and alkyl having 1 to 12 carbon atoms;

$n$ is a whole number 1 through 4;

$Z_1$ through $Z_8$ are substituents each selected from the group which consists of alkyl, alkoxyl, carboxy, formyl, acyl, carboxy substituted by alkyl, carboxamido, hydroxyl, amino, nitro, halo, and sulfo;

$Y_1$ is selected from the group which consists of $-COOM_2$ and $-CN$;

$Y_2$ is selected from the group which consists of $-COOM_3$ and $-CN$; and $M_1$ through $M_4$ are selected from the group which consists of hydrogen ion, an alkali metal ion, ammonium and ammonium substituted by alkyl 1 to 4 times and to a compound of the following formula:

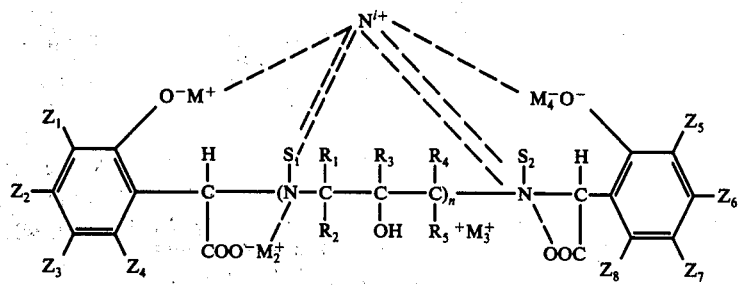

wherein:

$R_1$ through $R_5$ are each selected from the group which consists of hydrogen, methyl, ethyl and propyl;

$S_1$ and $S_2$ are each selected from the group which consists of hydrogen, $-CH_2CH_2OH$ and alkyl having 1 to 12 carbon atoms;

$n$ is a whole number 1 through 4;

$Z_1$ through $Z_8$ are substituents each selected from the group which consists of alkyl, alkoxyl, carboxy, formyl, acyl, carboxy substituted by alkyl, carboxamido, hydroxyl, amino, nitro, halo, and sulfo;

$M_1$ through $M_4$ are selected from the group which consists of hydrogen ion, an alkali metal ion, ammonium and ammonium substituted by alkyl 1 to 4 times.

N is a metal ion capable of chelating with the remainder of the above complex; and i is a whole number from 2 to 3.

Also, the processes for the preparation of the compounds are disclosed.

(a) A process for the preparation of a compound of the formula:

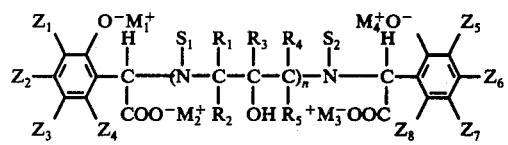

wherein $R_1$ through $R_5$ are each selected from the group which consists of hydrogen, methyl, ethyl and propyl;

$S_1$ and $S_2$ are each selected from the group which consists of hydrogen, —$CH_2CH_2OH$ and alkyl having 1 to 12 carbon atoms;

n is a whole number 1 through 4;

$Z_1$ through $Z_8$ are substituents each selected from the group which consists of alkyl, alkoxy, carboxy, formyl, acyl, carboxy substituted by alkyl, carboxamido, hydroxyl, amino, nitro, halo and sulfo; and $M_1$ through $M_4$ are each selected from the group which consists of hydrogen ion, an alkali metal ion, ammonium and ammonium substituted by alkyl 1 to 4 times which comprises the following: reacting a compound of the following formula:

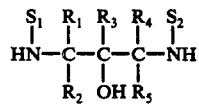

simultaneously with a compound of the formula:

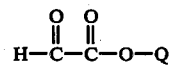

and simultaneously as well with a compound of the formula:

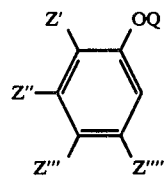

wherein Z', Z'', Z''', Z'''' are each any of $Z_1$ to $Z_8$ and Q is any of $M_1$ to $M_4$ and, (b) A process for the preparation of a compound of the formula:

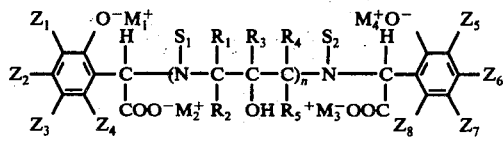

wherein $R_1$ through $R_5$ are each selected from the group which consists of hydrogen, methyl, ethyl and propyl;

$S_1$ and $S_2$ are each selected from the group which consists of hydrogen, —$CH_2CH_2OH$ and alkyl having 1 to 12 carbon atoms;

n is a whole number 1 through 4;

$Z_1$ through $Z_8$ are substituents each selected from the group which consists of alkyl, alkoxyl, carboxy, formyl, acyl, carboxy substituted by alkyl, carboxamido, hydroxyl, amino, nitro, halo and sulfo; and $M_1$ through $M_4$ are each selected from the group which consists of hydrogen ion, an alkali metal ion, ammonium and ammonium substituted by alkyl 1 to 4 times which comprises the following steps:

(a) reacting a compound of the following formula:

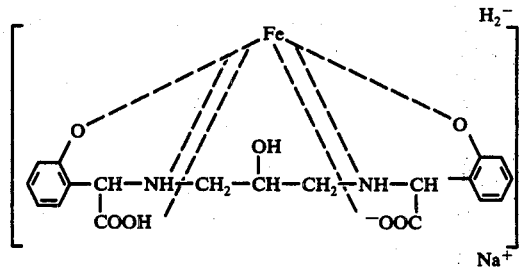

in which $R_1$ through $R_5$ are as defined above simultaneously with the compounds of the formula

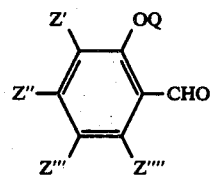

wherein Z', Z'', Z''', and Z'''' are any of $Z_1$ through $Z_8$ and Q is any of $M_1$ to $M_4$ to yield a compound of the formula:

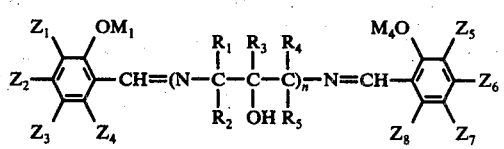

wherein $Z_1$ through $Z_8$, $R_1$ $R_5$, n, and $M_1$ and $M_2$ are as defined above and (b) reacting the above compound simultaneously with compounds of the formulae $S_1CN$ and $S_2CN$ to yield a compound of the following formula:

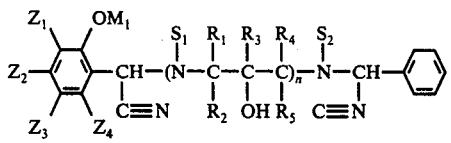

wherein $S_1$ and $S_2$, $R_1$ through $R_5$, $Z_1$ through $Z_8$ and $M_1$ and $M_4$ are as defined above; and (c) hydrolyzing the above compound in an aqueous solution containing $M_2$ and $M_3$ as cations to yield the desired product.

Also, each of the processes disclosed may further include the step of chelating the formed compounds with a metal cation with a valence of either 2+ or 3+ and which is capable of chelating. The $Fe^{2+}$ and $Fe^{3+}$ species are prime examples of chelating ions that may be employed here and a preferred pH range would be from about 3.0 to about 10.0. However, this range of pH is by no means the maximum range of the chelating power of the disclosed compounds.

With regard to the definition of each of the moieties of the disclosed compounds, there are the following preferences. $R_1$ through $R_5$ may be any of hydrogen, methyl, ethyl, n-propyl or isopropyl. All other alkyl groups herein may contain from 1 to 12 carbon atoms and preferably from 1 to 5 carbon atoms. The alkoxyl groups herein also contain from 1 to 12 carbon atoms and preferably from 1 to 5 carbon atoms. The acyl groups disclosed herein also contain from 1 to 12 and preferably 1 to 5 carbon atoms. The amine disclosed may be unsubstituted, or mono- or disubstituted by alkyl groups containing from 1 to 12 and preferably 1 to 5 carbon atoms. The same holds true for the carboxamido's amine function. The halo group may be fluorine, chlorine, bromine or iodine. The sulfo group may be unsubstituted or substituted by alkyl with 1 to 12 and preferably 1 to 5 carbon atoms. Also, the cations, $M_1$ through $M_4$ may be hydrogen, alkali metal: $Li+$, $Na+$, $K+$, $Rb+$, $Cs+$, ammonium or ammonium substituted by 1 to 4 alkyl groups each containing from 1 to 12 and preferably 1 to 5 carbon atoms. Where $M_1$ through $M_4$ will be discussed herein collectively, that group will be referred to as Q. Also, where a particular ring substituent can be any of $Z_1$ through $Z_8$, that substituent will be referred to as Z', Z" etc.

METHOD WITH GLYOXYLIC ACID

This procedure consists of reacting two gram-molecules of an alkaline gloxalate with two gram-molecules of phenol carrying the substituent groups desired with one gram-molecule of the amine. The reaction is generally carried out in alcohol or in an alcohol-water mixture, such that the reaction takes place in a homogeneous medium, at a temperature of about 70° to 100° C, generally corresponding to the boiling-point of the reacting alkaline mixture of a pH usually between 9 and 10.

In most cases the chelating product so obtained is recovered in an acid form, after acidifying the reaction product to a pH of 4 to 5, distillation, and/or addition of a solvent facilitating precipitation of the chelating agent. Likewise it can be helpful to eliminate the unreacted phenolic component by liquid/liquid extraction.

The metallic complexes are prepared by adding one gram-molecule of the acid or one of its salts as specified above, to one gram-molecule of the chosen metal, usually taken in the form of hydroxide, oxide, or salt, the reaction generally being carried out in water or in a mixture containing water.

METHOD WITH HYDROCYANIC ACID

This method takes place in four spearate steps which can be completed without needing at any time to isolate the product obtained, and this is the preferred method of manufacturing the chelating agents which are the subject of the invention.

(a) The first step consists of the action of one molecule of diamine on two molecules of the selected hydroxyaldehyde, with the desired substitutions on the benzene ring. The substituent groups on the nitrogen atoms are replaced by hydrogen in cases where $S_1$ and $S_2$ are a hydroxyethyl or hydroxypropyl group, the oxyethylenation or oxypropylenation not taking place until later.

(b) The second stage consists in the addition of a molecule of hydrocyanic acid to each CH group of the imine functions present, i.e. two cyanogen groups per molecule of di-imine. This reaction can take place in an anydrous environement; with hydrocyanic acid about 10% in excess of stoichiometery; in the presence of a second solvent miscible in the solvent used for the reaction, or at least soluble in it, in which the nitrile formed is soluble, so that the reaction can be carried out in a homogeneous environment; and in presence of a mineral or organic acid serving as catalyst for the reaction.

(c) The third step consists in the direct hydrolysis of the product of the preceding reaction, which is very easily carried out and gives the di-acid directly, even with commercial hydrochloric acid, i.e. containing 36 to 37% of HCl in solution in water, without its being necessary to use a stronger acid which is inconvenient to handle. The operation is preferably carried out under reflux conditions at the same time as the azeotropic elimination of solvent and the excess of hydrocyanic and hydrochloric acids. It can also be conducted without distilling off the excess hydrocyanic acid to elimination, the toluene being separated from the aqueous phase containing the acid by decantation after cooling.

(d) The fourth stage concerns the preparation of the metallic complex, which is effected by adding to the above aqueous phase a quantity of metal stoichiometrically calculated: one molecule of amine to one atom of metal. The metal can be added in any form, but preferably as a hydroxide or a salt, according to the suitability of the raw materials available, and this without any need to isolate the acid. The pH of the complex is then adjusted to the desired value by salification with an alkali metal, ammonia, or a nitrogenous base.

The following Examples serve to illustrate the procedures which have just been described.

EXAMPLE 1

In a glass flask of 2 liters capacity are placed:
195 gm. of dry glyoxylic acid with 77.5% active material
100 gm. of water
204 gm. of 40% soda solution in water
90 gm. of 1,3-diamino-isopropanol
210 gm. of phenol
150 ml. of methanol.

The pH obtained is 8.5 - 8.6

The mixture is heated to reflux temperature and the pH is adjusted to 8.5 with a very small quantity of soda.

After 6 hours of reflux distillation the solution is cooled, and then three extractions are carried out with 100 ml. of diethylether to eliminate the unreacted phenol.

The aqueous phase is then brought to pH of 4 by addition of hydrochloric acid.

The solution is concentrated under vacuum at a temperature of less than 50° C, and the liquid obtained is treated with acetone, which causes the separation of a viscous oil which, after agitation with methanol, crystallizes and can be filtered out. After filtration the product obtained is dried. Under vacuum at low temperature one obtains 453 gm. of a solid containing 75.6% of dry material and 24.4% of sodium chloride, i.e. a total yield of 80%.

100 gm. of this product, after an identical recrystallization, gives 82 gm. of a yellowish powder containing 89.6% of dry material and 6.22% of nitrogen in amine form (by quantitative determination of the perchloric acid in a non-aqueous medium) and has analytically determined molecular weight of 402 (theoretical molecular weight 392) corresponding to the formula:

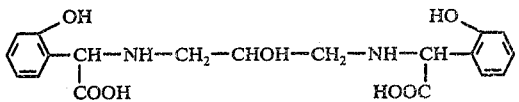

In another way, by spectrophotometric titration at a pH of 5.2 with a solution of 100 mg. ferric iron per liter a molecular weight of 398 was determined.

Furthermore, the wavelength and intensity of the absorption maxima were measured for 1/1 ferric complexes (1 gm. atom of iron for 1 gm. molecule of sequestrant) as a function of pH (A), and this was compared with results obtained under the same conditions with ethylene-bis-($\alpha$ imino-2-hydroxy) — phenylacetic acid (B).

| pH: | 3.0 | 3.1 | 3.4 | 4.4 | 4.6 | 5.6 | 6.5 | 7.5 | 8.5 | 9.5 | 10.3 |
|---|---|---|---|---|---|---|---|---|---|---|---|
| A $\lambda$ in mm. | | 495 | | | 480 | | 475 | 470 | 470 | 430 | 415 |
| Intensity | | 182 | | | 197 | | 200 | 219 | 216 | 210 | 193 |
| B $\lambda$ in mm. | | | | | | | | | | | |
| Intensity | 500 | | 490 | 475 | | 475 | 475 | 478 | 460 | 445 | |
| | 124 | | 150 | 161 | | 164 | 164 | 166 | 149 | 147 | |

From the above table it is evident that the color intensity of the complex only diminishes after the pH of the hydroxylized product exceeds 9.5, whereas for product B the color intensity decrease starts from pH 8.5.

This analysis demonstrates that the introduction of the central hydroxyl group has increased the existence range of the complex towards high pH values.

EXAMPLE 2

In a flask of 1 liter capacity, equipped with a stirrer and a condenser, are mixed:
475 gm. toluene
45 g. 1,3-diamino-isopropanol
and it is heated to reflux temperature.

After about 20 minutes 122 gm of salicylic aldehyde are added, which reduces the reflux temperature to 94° C.

The water formed is then distilled off azeotropically and a bright yellow solution is obtained which, on cooling, allows the recovery of 138 gm. of 1,3-bis-(salicylide-amino)propanol-2 of formula:

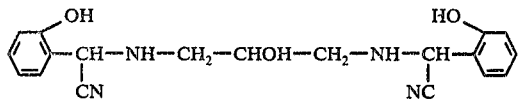

i.e. a yield of 92.5%.

The evaporation of solvent causes yellow cyrstals to appear, identical with the above, bringing the yield to 99%.

EXAMPLE 3

The 1,3-bis-(salicylide-amino)propanol-2 is prepared as in Example 2, but without separating the crystals. On cooling, with agitation, crystallization commences at 11° C.

2.25 gm. of acetic acid and 300 ml. of methanol are added, which has the effect of dissolving the crystals and rendering the mixture homogeneous.

Then 41.2 ml. of hydrocyanic acid are rapidly added at 0° C and heated to 30° C, a temperature that is maintained for two hours to achieve the formation of a nitrile of the formula:

Then 600 gm. of commercial hydrochloric acid (35 – 36% aqueous solution) are added and progressively heated to the reflux temperature which is around 70° C, a temperature that is maintained for 30 minutes; the reaction mixture is then distilled until the liquid reaches 82° – 83° C, which requires the distillation of 250 gm. of liquid, the last drops of which contain practically no hydrocyanic acid.

Then concentration takes place under vacuum at a temperature not exceeding 50° C until the residual volume is about 500 ml., then 135 gm. of ferric chloride hexahydrate dissolved in the same weight of water are added, and the pH is adjusted to 6.5 with the help of an aqueous solution of sodium.

The product obtained is dried in a sieve and gives 560 gm. of a brownish-violet powder the spectrophotometric analysis of which shows that it contains more than 35.5% of active material expressed as monosodium ferric complex of 1,3-diaminol-isopropanol-bis-(o-hydroxyphenyl-acetic) acid of formula:

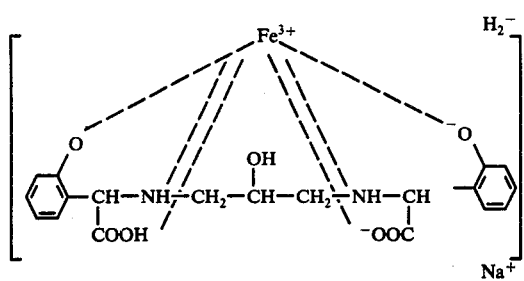

a complex the acid of which has the formula:

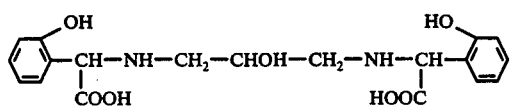

i.e. a yield of more than 85%.

EXAMPLE 4

The same procedures and reaction conditions of Example 1 were employed except that $Z_1$ through $Z_8$, the phenol substitutents were substituted by methyl, ethoxy, carboxy, formyl, acetyl, carboxy substituted by methyl, carboxamido N,N substituted by methyl, hydroxyl, amino, nitro, chloro, and sulfo in successive tests.

EXAMPLE 5

The same procedures and reaction conditions as Example 1 were employed except that $M_1$ through $M_4$, the cation substituents were sodium, ammonium and dimethyl ammonium.

EXAMPLE 6

The same procedures and reaction conditions of Example 1 were employed except that $R_1$ through $R_5$ were ethyl.

EXAMPLE 7

The same procedures and reaction conditions as in Example 3 were employed except that $CH_3CN$ and $NCCH_2CH_2OH$ were employed as the addition compounds instead of HCN.

As is self-evident, the invention is not limited solely to the chelation agents, metallic chelates and their derivatives as described above by way of example; it encompasses, on the contrary, all products having the structure given by formula (1).

I claim:

1. A process for preparing a compound of the following formula:

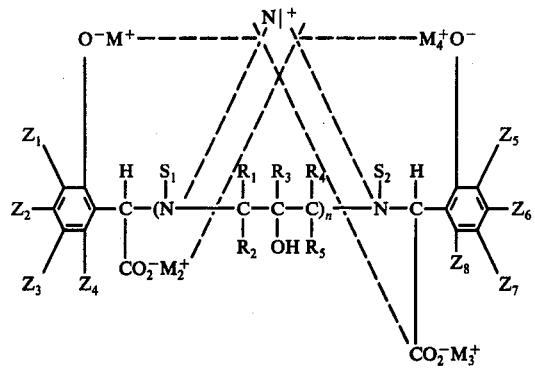

wherein
$R_1$ through $R_5$ are each selected from the group which consists of hydrogen, methyl, ethyl and propyl;
$S_1$ and $S_2$ are each selected from the group which consists of hydrogen, $-CH_2CH_2OH$ and alkyl having 1 to 12 carbon atoms;
$n$ is a whole number 1 through 4;
$Z_1$ through $Z_8$ are substituents each selected from the group which consists of alkyl, alkoxyl, carboxy, formyl, acyl, carboxy substituted by alkyl, carboxamido, hydroxyl, amino, nitro, halo, and sulfo;
$M_1$ through $M_4$ are selected from the group which consists of hydrogen ion, an alkali metal ion, ammonium and ammonium substituted by alkyl 1 to 4 times;
N is divalent or trivalent iron of the above complex; and which comprises:
reacting a compound of the following formula:

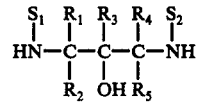

simultaneously with a compound of the formula:

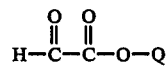

and simultaneously as well with a compound of the formula:

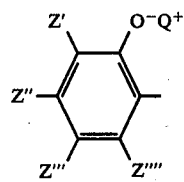

wherein $Z'$, $Z''$, $Z'''$, $Z''''$ are each any of $Z_1$ to $Z_8$ and Q is any of $M_1$ to $M_4$; and
chelating the resultant compound with iron with a valence of $2^+$ or $3^+$ and capable of chelating.

* * * * *